(12) United States Patent
Morningstar et al.

(10) Patent No.: US 7,938,770 B2
(45) Date of Patent: May 10, 2011

(54) PENILE PROSTHESIS, PENILE PROSTHESIS INSERTION TOOL AND SYSTEM THEREOF

(75) Inventors: Randy L. Morningstar, Brooklyn Park, MN (US); Egon Triel, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/783,785

(22) Filed: May 20, 2010

(65) Prior Publication Data
US 2011/0071345 A1    Mar. 24, 2011

(30) Foreign Application Priority Data
Sep. 22, 2009  (DK) ................................ 2009 70120

(51) Int. Cl.
*A61F 5/00* (2006.01)
(52) U.S. Cl. .......................................................... 600/40
(58) Field of Classification Search .............. 600/38–41; 128/897, 898
See application file for complete search history.

(56) References Cited

U.S. PATENT DOCUMENTS

| 4,590,927 | A | | 5/1986 | Porter et al. |
| 4,653,485 | A | * | 3/1987 | Fishell ............................ 600/40 |
| 5,484,450 | A | | 1/1996 | Mohamed |
| 7,066,878 | B2 | * | 6/2006 | Eid ................................. 600/40 |
| 7,169,103 | B2 | | 1/2007 | Ling et al. |
| 7,172,602 | B2 | * | 2/2007 | George et al. ................. 606/108 |
| 2004/0225182 | A1 | | 11/2004 | Eid |

FOREIGN PATENT DOCUMENTS
WO         03/701970 A1    9/2003
* cited by examiner

*Primary Examiner* — Samuel G Gilbert
(74) *Attorney, Agent, or Firm* — Coloplast Corp., Coloplast A/S; Daniel G. Chapik; Nicholas R. Baumann (57) ABSTRACT

An implantable penile prosthesis system includes a penile prosthesis and an insertion tool. The penile prosthesis includes a cylinder extending between a distal tip and a proximal tip. At least one of the distal tip and the proximal tip has a pocket accessible by an opening, where the pocket is formed to extend laterally beyond a perimeter of the opening. The insertion tool extends between a distal end and a proximal end and includes an expansion mechanism coupled to the distal end. The opening in the tip(s) is sized to receive the distal end of the insertion tool and the expansion mechanism is configured to expand into the pocket to couple the insertion tool with the penile prosthesis.

28 Claims, 11 Drawing Sheets

PENILE PROSTHESIS, PENILE PROSTHESIS INSERTION TOOL AND SYSTEM THEREOF

BACKGROUND

Implanted penile prostheses provide relief for men with erectile dysfunction.

In a typical implantation procedure, the penis of the patient is incised to expose the corpora cavernosa that are aligned axially in a side-by-side orientation within the penis. Each corpora cavernosum is dilated, for example by introducing gradually larger stainless steel rods into the corpora cavernosum until a space is created that is sized to receive a cylinder of the penile prosthesis. The cylinder is typically provided with a traction suture attached to its distal end. A tool (e.g., a "Furlow" introducer) is introduced into the space formed in the corpora cavernosum to guide a needle (e.g., a "Keith" needle) attached to the traction suture through a distal surface of the glans penis. The needle and the suture are subsequently passed through the glans penis to pull the cylinder of the penile prosthesis to a distal location within the corpora cavernosum, which locates the distal end of the prosthesis approximately mid-glans. Although the above-described approach has proven effective in treating erectile dysfunction, the needle forms a lesion in the glans penis, which can cause bleeding and discomfort to the patient.

SUMMARY

One aspect provides an implantable penile prosthesis system including a penile prosthesis and an insertion tool. The penile prosthesis includes a cylinder extending between a distal tip and a proximal tip. At least one of the distal tip and the proximal tip has a pocket accessible by an opening, where the pocket is formed to extend laterally beyond a perimeter of the opening. The insertion tool extends between a distal end and a proximal end and includes an expansion mechanism coupled to the distal end. The opening in the tip(s) is sized to receive the distal end of the insertion tool and the expansion mechanism is configured to expand into the pocket to couple the insertion tool with the penile prosthesis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Soft tissue includes dermal tissue, sub-dermal tissue, ligaments, tendons, or membranes but does not include bone.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

The typical penile prosthesis is implanted by passing a needle/suture through the glans penis to direct/pull the prosthesis distally into the corpora cavernosum. For example, conventional penile prostheses have a suture attached to a suture hole formed in a distal end of the prosthesis, where the suture is configured to be passed through the glans penis to assist in inserting the prosthesis distally into the corpora cavernosum. In contrast, a sutureless penile prosthesis as described and provided for herein is implanted without passing a needle/suture through the glans penis. The sutureless penile prostheses of this specification are implanted into a distal end of the corpora cavernosum with a tool that includes a distal end provided with an expansion mechanism that expands to gain traction with the prosthesis which allows the prosthesis to be pushed or directed into the distal end of the corpora cavernosum without passing a suture or a needle through the glans penis.

A cannula is a tube, meaning a rod-like device having an axial bore passing longitudinally through the rod-like device.

Embodiments provide a system for the sutureless implantation of a penile prosthesis including an insertion tool having an expansion mechanism that is extensible out of and away from a distal end of the tool. Activation of the expansion mechanism results in the insertion tool positively engaging with the penile prosthesis to provide a suitable level of traction to the prosthesis for implantation into the male penis. After implantation, the expansion mechanism is configured to deflate for retraction, which allows the tool to be removed from the penis with low or reduced friction between the insertion tool and tissue of the penis. Consequently, the insertion tool may be advantageously removed from the penis without disturbing the prosthesis that has been implanted into the penis.

Figure 1:
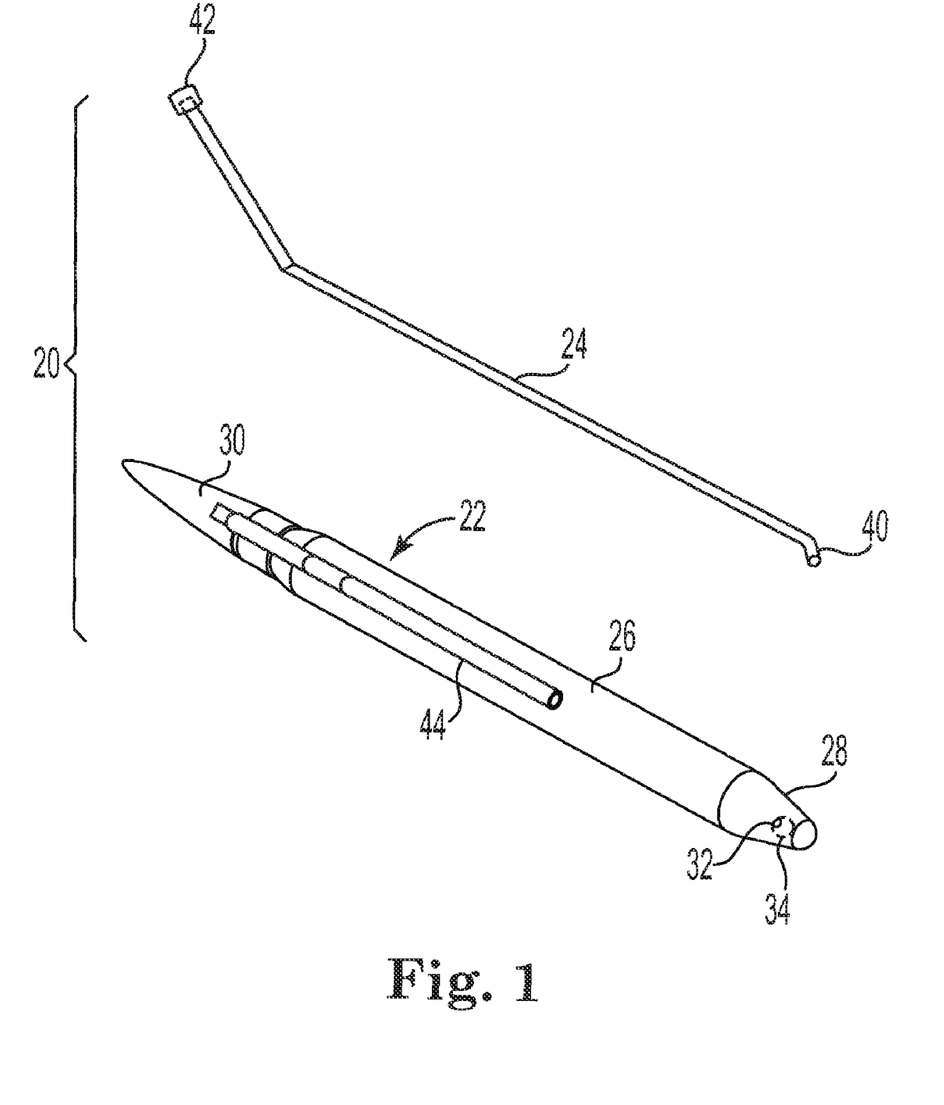
FIG. 1 is a perspective view of a system including an insertion tool configured to implant a penile prosthesis into a male patient according to one embodiment.

FIG. 1 is a perspective view of a system 20 for implanting a penile prosthesis according to one embodiment. System 20 includes an implantable penile prosthesis 22 (IPP 22) and an insertion tool 24 configured to place IPP 22 into a corpora cavernosa of the patient.

In one embodiment, IPP 22 includes a cylinder 26 extending between a distal tip 28 and a proximal tip 30, where at least one of the distal tip 28 and the proximal tip 30 includes an opening sized to receive insertion tool 24. For example, in one embodiment distal tip 28 is provided with an opening 32 sized to receive insertion tool 24, the opening 32 communicates with a pocket 34 that is formed within distal tip 28, where the pocket 34 is configured to couple with an expansion mechanism that is deployed from tool 24. In one embodiment, each of the distal tip 28 and proximal tip 30 is provided as a tapered tip that terminates in a smoothly rounded tip end.

Tool 24 is configured to engage with one or both of the end caps 28, 30 individually to facilitate implanting IPP 22 into a distal end of the corpora cavernosum of the patient without the use of a suture and without perforating the glans penis. In an exemplary embodiment, tool 24 is provided as a cannula that extends between a distal end 40 and a proximal end 42 and includes an expansion mechanism (not shown) disposed within distal end 40 of the cannula of tool 24. The expansion mechanism is configured to selectively move between a first state in which the expansion mechanism is retracted into distal end 40 and a second state in which expansion mechanism expands out of and away from a distal end 40 of tool 24. In one embodiment, proximal end 42 of tool 24 includes a Luer-lock or other suitable connector that is configured to couple with a fluid source, such as saline delivered through some form of tubing attached to a pump.

In another embodiment, proximal end 42 of tool 24 defines a closed diaphragm that is configured to receive an inflation needle from a syringe or other such manual inflation mechanism, where the manual injection of fluid through the diaphragm pressurizes/activates the expansion mechanism to move the expansion mechanism out of the distal end 40 of tool 24.

In one embodiment, cylinder 26 is provided as inflatable cylinder. In general, it is desirable to deflate cylinder 26 in preparation for implantation of IPP 22 into the penis, since the deflated cylinder 26 is easier to insert into the corpora cavernosum. The cylinder 26 is configured to be subsequently inflated by the surgeon to ensure performance of IPP 22, and later after healing by the patient to achieve an erection. The inflatable cylinder 26 is generally provided as an oblong cylinder that is closed at its distal end (e.g., the end to which distal tip 28 is attached) and closed at it proximal end when proximal tip 30 is attached. When so assembled, cylinder 26 is sealed and configured to be inflated when liquid (e.g., saline typically, or a gas) is introduced into tubing 44.

In one embodiment, inflatable cylinder 26 is fabricated from a urethane material sold under the trademark Bioflex and is available from Coloplast Corp., Minneapolis, Minn. Distal tip 28 is attachable to the distal end of cylinder 26. In one embodiment, distal tip 28 is formed from silicone, which is dissimilar to the urethane material of the Bioflex cylinder 26. To facilitate the attachment of these two dissimilar materials, in one embodiment the urethane material of cylinder 26 is coated with fumed silica to prepare the urethane surface for bonding with the silicone tip 28.

Alternatively, in one embodiment distal tip 28 is integrally formed on the distal end of cylinder 26 as a one-piece unit.

One or both of distal tip 28 and proximal tip 30 are formed to include an internal pocket 34 that communicates with opening 32, where opening 32 is sized to receive distal end 40 of tool 24 and the expansion mechanism is configured to expand into and couple with pocket 34 such that tool 24 develops traction useful for implanting IPP 22 into the patient.

Figure 2:
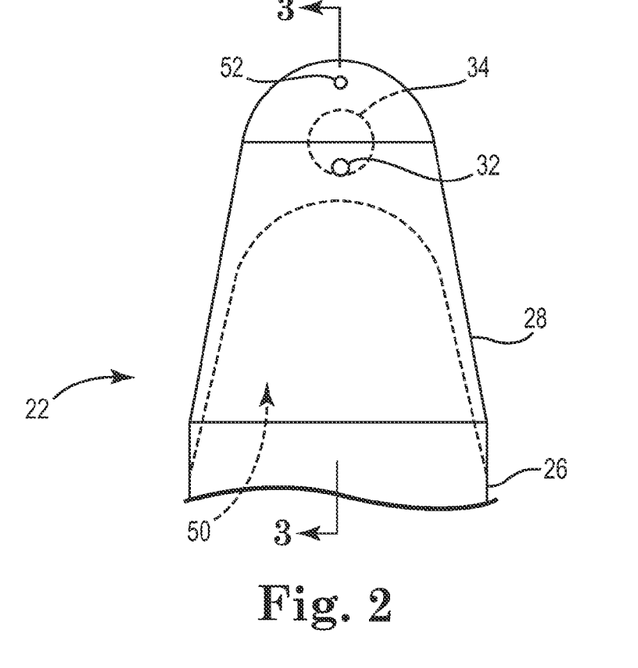
FIG. 2 is a side view of a distal tip of the penile prosthesis illustrated in FIG. 1.
Figure 3:
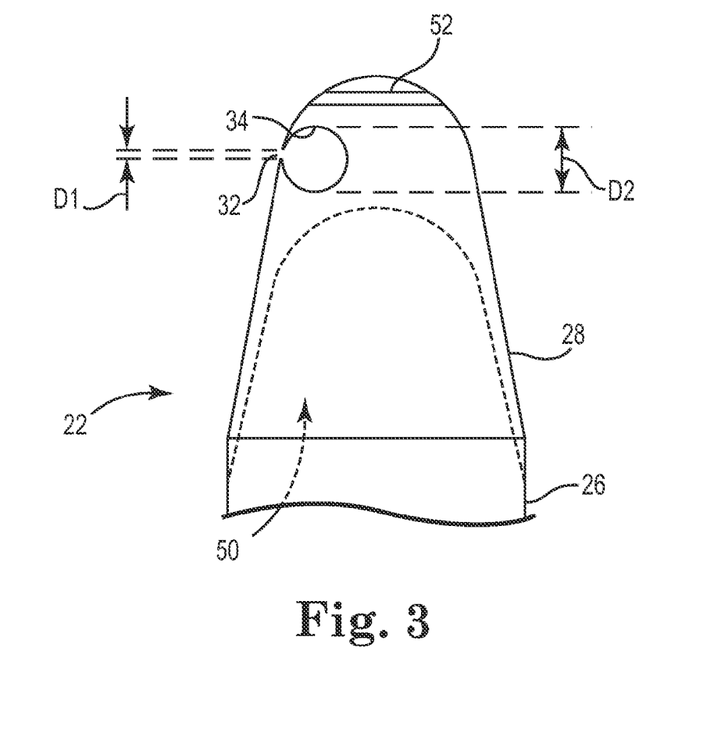
FIG. 3 is a cross-sectional view of the distal tip illustrated in FIG. 2.

FIG. 2 is a side view and FIG. 3 is a cross-sectional view of distal tip 28. The view of FIG. 3 is taken through line 3-3 illustrated in FIG. 2. In one embodiment, distal tip 28 is formed (e.g., injection molded or transfer molded as examples) from a polymer to define a cavity 50 that is sized to be placed over the exterior distal end of cylinder 26. In one embodiment, distal tip 28 is formed from silicone and is attached to cylinder 26.

Opening 32 is formed in distal tip 28 and communicates with pocket 34. In one embodiment, opening 32 is provided with a dimension D1 and pocket 34 has a dimension D2, where dimension D2 is greater than dimension D1. In one embodiment, the dimension D2 is approximately two times greater than the dimension D1 such that pocket 34 has a boundary that extends laterally beyond a perimeter of opening 32. In one embodiment, the dimension D2 is at least three times greater than the dimension D1 such that pocket 34 extends laterally well beyond a perimeter of opening 32.

In one embodiment, pocket 34 is formed as a substantially spherical space inside distal tip 28 having a diameter D2, and opening 32 is provided as a circular opening that is smaller than pocket 34 and has a diameter D1. As illustrated in FIG. 3, in one embodiment the opening has a diameter D1 and the pocket 34 defines a spherical recess having a width and a height and a depth of D2, where D2 is greater than D1. In one embodiment, the pocket 34 is a non-spherical recess where at least one of the pocket's 34 width and the pocket's 34 height is sized to be approximately two times larger than the diameter of the opening D1. Suitable exemplary dimensions for opening 32 and pocket 34 include the dimension D1 provided in a range between 0.5-1.0 mm and dimension D2 provided in a range between 2-6 mm.

IPP 22 is configured to cooperate with tool 24 to allow sutureless implantation of IPP 22 into a corpora cavernosum of the patient. However, some surgeons desire to have the option of placing a penile prosthesis distally within the penis via a suture that is employed to guide cylinder 26 distally forward within the penis. With this in mind, in one embodiment an optional suture hole 52 is formed horizontally to extend through distal tip 28 to permit the surgeon to place the prosthesis in a manner that s/he has become accustomed to should the surgeon opt not to employ tool 24.

Figure 4:
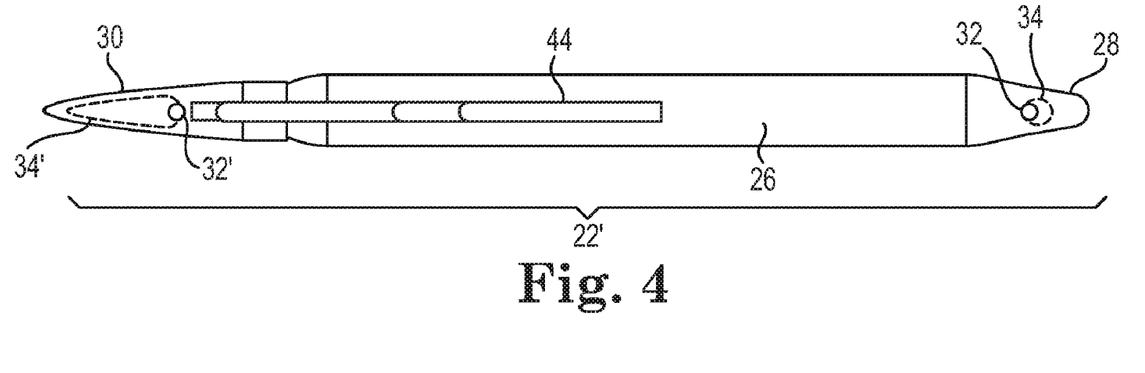
FIG. 4 is a side view of a penile prosthesis including openings formed in the distal tip and a proximal tip that are sized to receive the insertion tool illustrated in FIG. 1.

FIG. 4 is a side view of another embodiment of an implantable penile prosthesis 22' (IPP 22'). IPP 22' includes distal tip 28 formed to include opening 32 communicating with pocket 34 and proximal tip 30 including a separate opening 32' communicating with a pocket 34'. Each opening 32, 32' is sized to receive distal end 40 of tool 24 (FIG. 1). Each pocket 34, 34' is configured to engage with an expansion mechanism that expands out from distal end 40 of tool 24. In this manner, tool 24 is configured to engage with and insert distal tip 28 into a distal end of the corpora cavernosum of the patient, and after decoupling tool 24 from tip 28, tool 24 is configured to engage with and insert proximal tip 30 into a proximal end of the corpora cavernosum of the patient.

Figure 5:
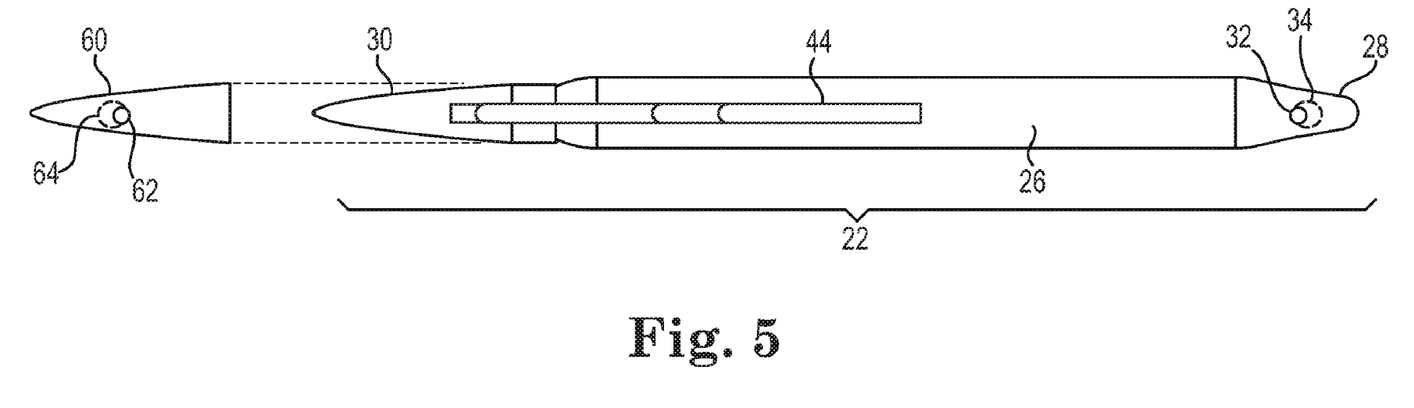
FIG. 5 is a side view of a rear tip extender attachable to a penile prosthesis, where the rear tip extender includes an opening sized to receive the insertion tool illustrated in FIG. 1.

FIG. 5 is a side view of IPP 22 and a rear tip extender 60 configured to be attached to proximal tip 30 according to one embodiment. Patients have different anatomical sizes and it is desirable to provide IPP 22 with additional length to better fit IPP 22 proximally into the corpora cavernosum of the patient. To this end, in one embodiment rear tip extender 60 is provided in a variety of lengths from about 0.5 cm-12 cm and is attachable to proximal tip 30 to extend an overall length of IPP 22. In one embodiment, rear tip extender 60 is provided with an opening 62 that communicates with a pocket 64, where these features are configured to cooperate with tool 24 to facilitate the sutureless insertion of IPP 22 into the patient. Opening 62 is similar to opening 32 described above and pocket 64 is similar to pocket 34 described above.

Figure 6A:
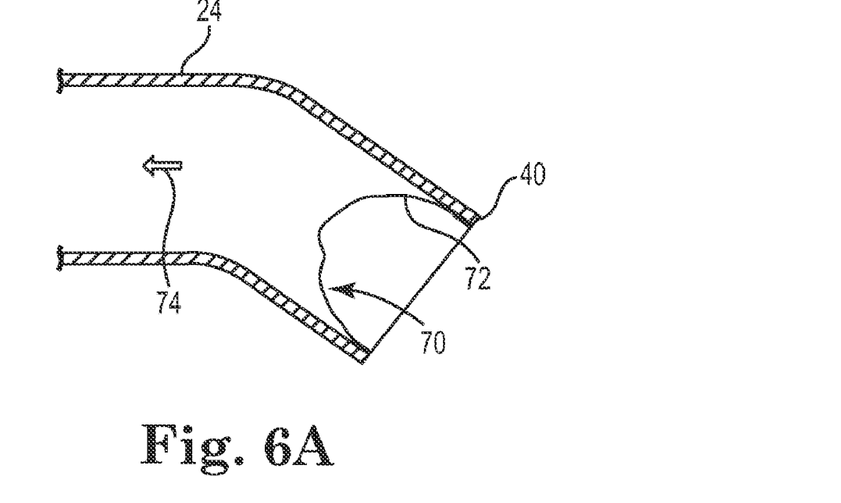
FIG. 6A is a cross-sectional view of a distal end of the insertion tool illustrating an expansion mechanism in a retracted state according to one embodiment.
Figure 6B:
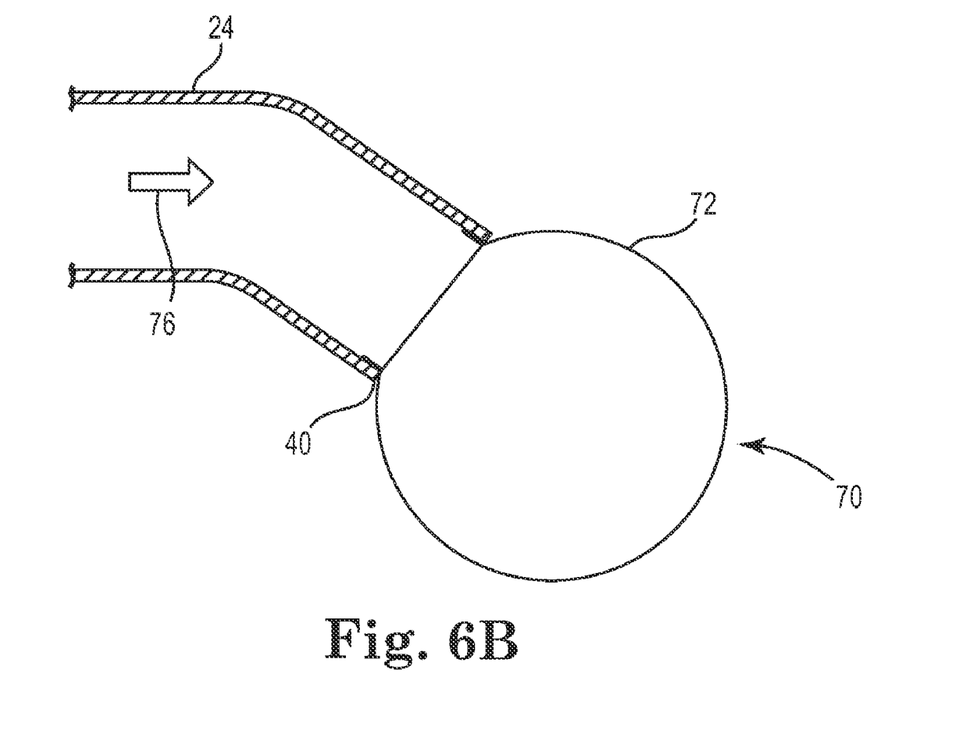
FIG. 6B is a cross-sectional view of the distal end of the insertion tool illustrating the expansion mechanism in an expanded state according to one embodiment.

FIG. 6A is a side cross-sectional view of an expansion mechanism 70 in a deflated/retracted state and FIG. 6B is a side cross-sectional view of expansion mechanism 70 in an expanded state. In one embodiment, expansion mechanism 70 is provided as elastic diaphragm attached to distal end 40 of tool 24. Expansion mechanism 70 is configured to expand laterally beyond distal end 40 in response to an activation force, such as air pressure, liquid pressure, or mechanical force supplied through the cannula of tool 24. In one exemplary embodiment, expansion mechanism 70 is provided as a balloon 72 connected to distal end 40 of tool 24. When suction or a negative force (represented at 74) is applied to the cannula of tool 24, expansion mechanism 70 is retracted inside the cannula (inside distal end 40). Conversely, when positive pressure is applied to the cannula as represented at 76, expansion mechanism 70 expands laterally out from and beyond the boundary of distal end 40 of tool 24. To this end, expansion mechanism 70 is configured to move beyond the boundary of distal end 40 of tool 24 to positively engage with pocket 34 (FIG. 3).

A variety of mechanism are suitable for selectively and controllably expanding expansion mechanism 70. For example, in one embodiment proximal end 42 of tool 24 (FIG. 1) includes a connector that is configured to receive fluid delivered at a suitable pressure to expand the expansion mechanism 70. One suitable such connector is a Luer-lock connector provided on the proximal end 42 of tool 24 that threads or couples to an air source or liquid source to inflate expansion mechanism 70.

Figure 6C:
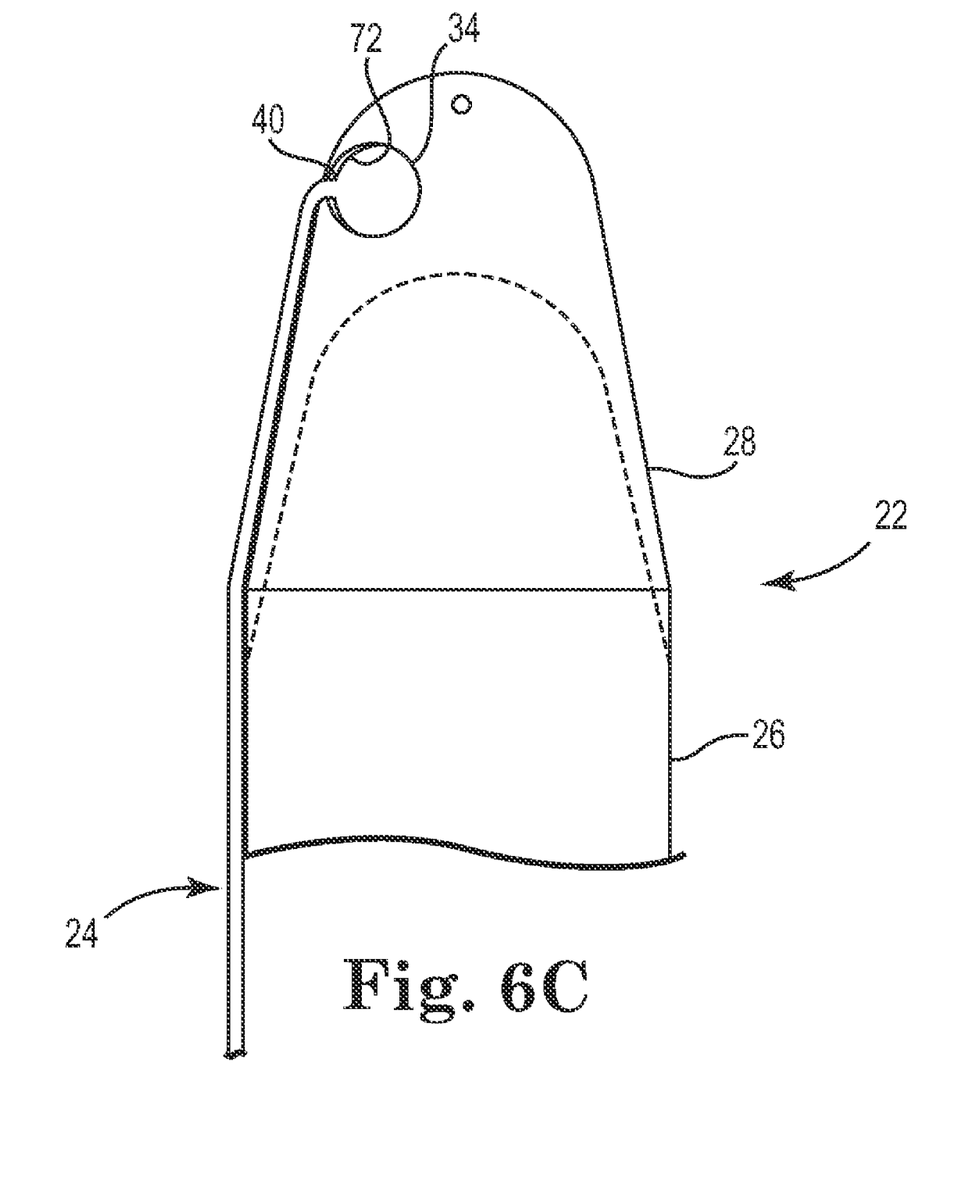
FIG. 6C is a schematic view of one embodiment of the expansion mechanism illustrated in FIG. 6B expanded into a pocket formed in the distal tip of the penile prosthesis illustrated in FIG. 2.

FIG. 6C is a schematic view of one embodiment of expansion mechanism 70 expanded into pocket 34 formed in distal tip 28 of the penile prosthesis. It is desirable that expansion mechanism 70 positively couple with pocket 34 to permit tool 24 to deliver force to IPP 22 of a sufficient magnitude to implant IPP 22 into the corpora cavernosum of the patient. To this end, in one embodiment the diaphragm or balloon 72 is fabricated from polyester and configured to rigidly couple within pocket 34 formed in distal tip 28. Balloon 72 is configured to be relatively rigid when inflated or expanded such that expansion mechanism 70 has sufficient strength when coupled with pocket 34 to allow tool 24 to guide IPP 22 into the corpora cavernosum of the patient. In one embodiment, balloon 72 is a polyester balloon configured to aggressively engage with pocket 34 formed into a silicone tip.

Figure 7A:
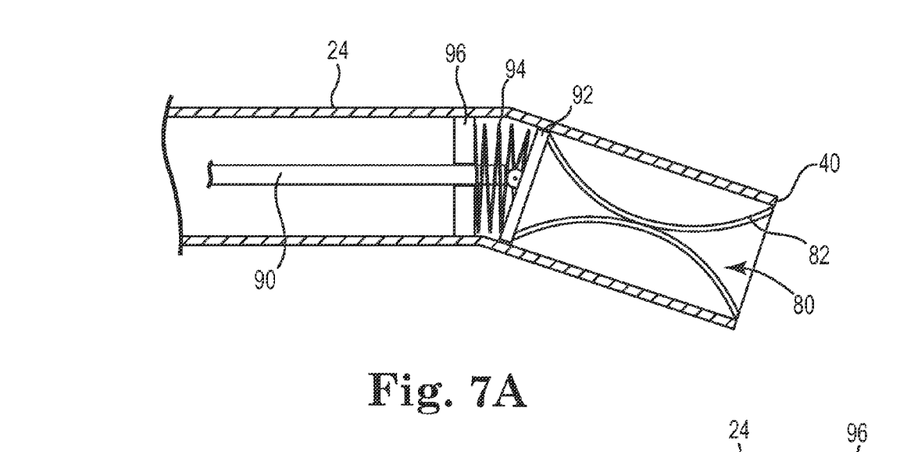
FIG. 7A is a cross-sectional view of a distal end of another embodiment of an insertion tool illustrating an expansion mechanism in a retracted state.
Figure 7B:
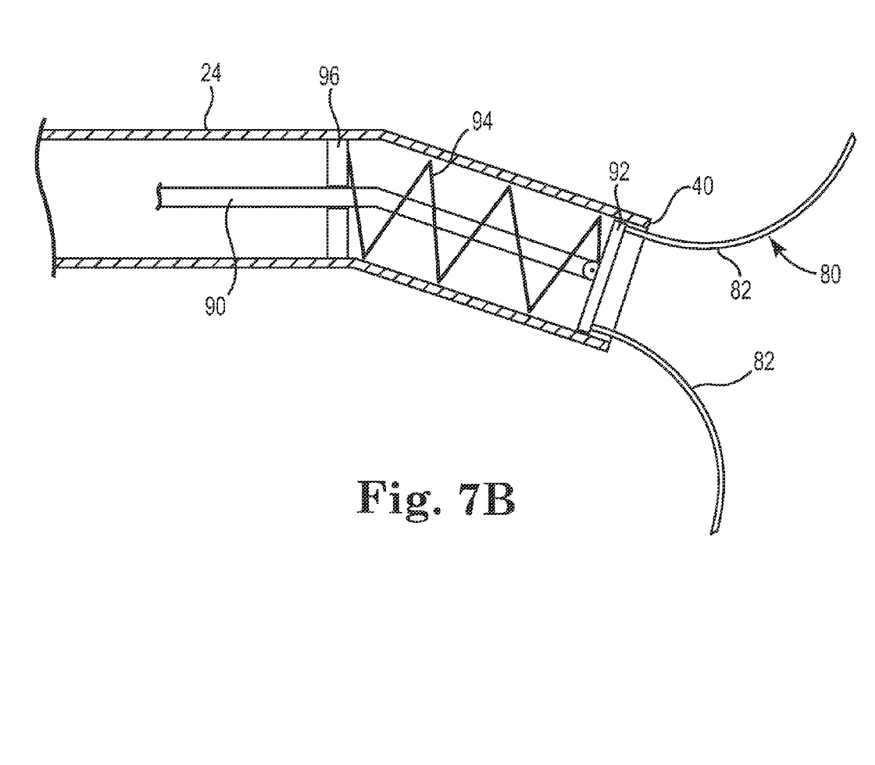
FIG. 7B is a cross-sectional view of the distal end of the insertion tool illustrated in FIG. 7 with the expansion mechanism in an expanded state.

FIG. 7A is a side cross-sectional view of another embodiment of an expansion mechanism 80 in a retracted state and FIG. 7B is a side cross-sectional view of expansion mechanism 80 in an expanded state. In one embodiment, expansion mechanism 80 is provided as a mechanical mechanism including at least one rigid and extensible finger 82 that is configured to move out of and laterally beyond a boundary of distal end 40 of tool 24.

In one embodiment, expansion mechanism 80 includes a push rod 90 disposed within the cannula of tool 24 that is coupled to a plunger 92, where the plunger 92 is biased by a spring 94 relative to a collar 96 that is likewise disposed within the cannula of tool 24. In one embodiment, push rod 90 is movably contained within the cannula of tool 24 and is configured to be manipulated by a trigger or other suitable device attached adjacent to proximal end 42 of tool 24. An opposing end of push rod 90 is coupled to plunger 92, for example by a pin or a pivot to allow push rod 90 to deflect along the curve of the distal end portion of tool 24. Spring 94 is connected between plunger 92 and collar 96. The distal movement of push rod 90 expands spring 94 and allows fingers 82 to move out of distal end 40 of tool 24. In one embodiment, fingers 82 are provided with a preset shape or curvature such that the fingers 82 expand laterally beyond the sides of distal end 40 when the fingers 82 exit tool 24, as best illustrated in FIG. 7B. Conversely, when push rod 90 is retracted in a proximal direction (with a force acting on push rod 90 is removed or a retraction force is applied to rod 90), spring 94 compresses to retract plunger 92 toward collar 96 which retracts fingers 82 back inside distal end 40 of tool 24. In this manner, tool 24 is provided with a mechanically movable and expanding mechanism that provides sufficient traction when coupled with pocket 34 to allow tool 24 to guide IPP 22 into the corpora cavernosum of the patient.

Figure 7C:
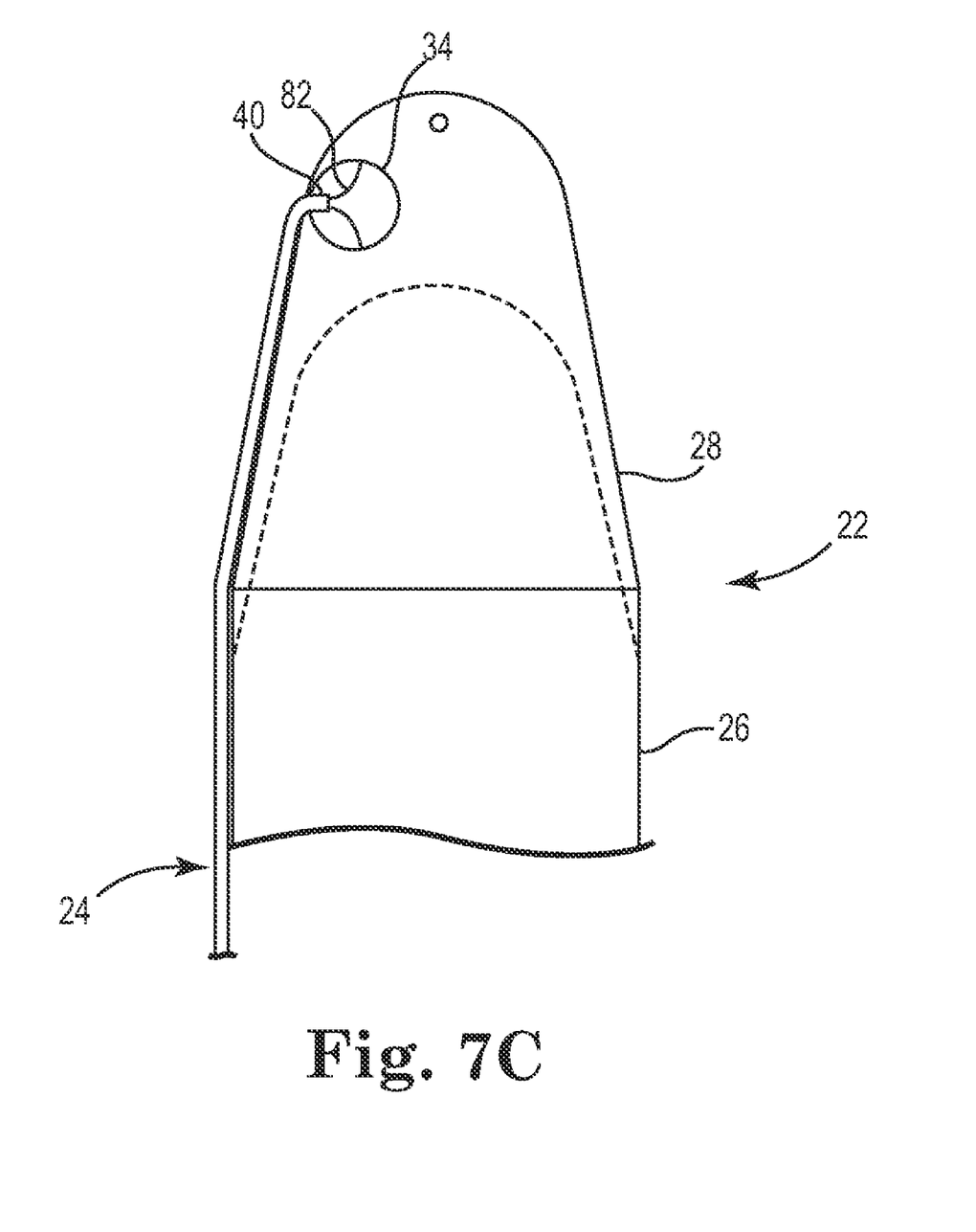
FIG. 7C is a schematic view of one embodiment of the expansion mechanism illustrated in FIG. 7B expanded into a pocket formed in the distal tip of the penile prosthesis illustrated in FIG. 2.

FIG. 7C is a schematic view of one embodiment of expansion mechanism 80 expanded into pocket 34 formed in distal tip 28 of the penile prosthesis. Mechanical expansion mechanism 80 is positively coupled with pocket 34 to permit tool 24 to deliver a forward pushing force to IPP 22 of a sufficient magnitude to implant IPP 22 into the corpora cavernosum of the patient. The expansion mechanism 80 is retractable back inside distal end 40 of tool 24 after placement of IPP 22 into the corpora cavernosum of the patient.

Figure 8:
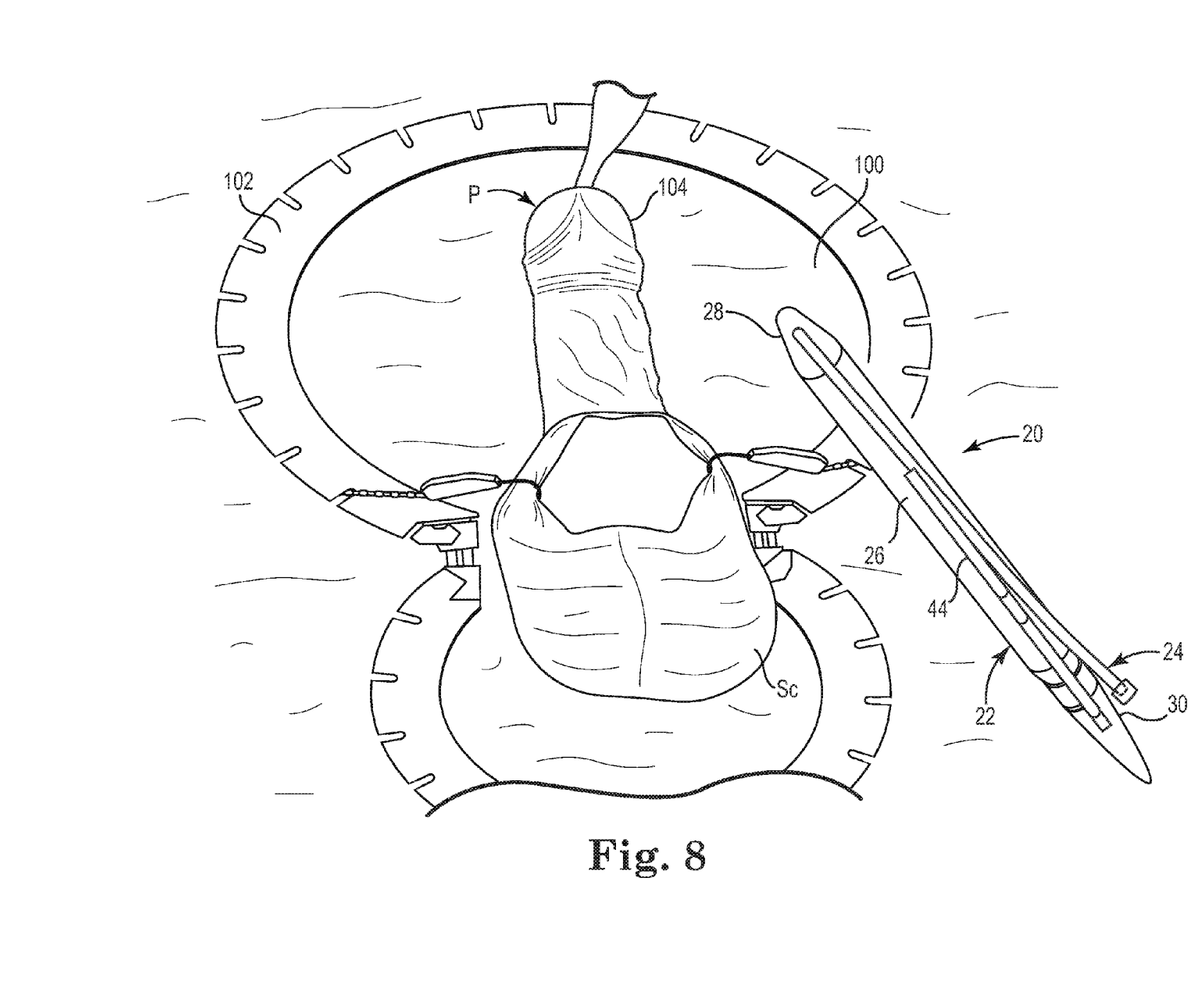
FIG. 8 is a schematic diagram of a patient prepped for the surgical implantation of the penile prosthesis illustrated in FIG. 1.
Figure 9:
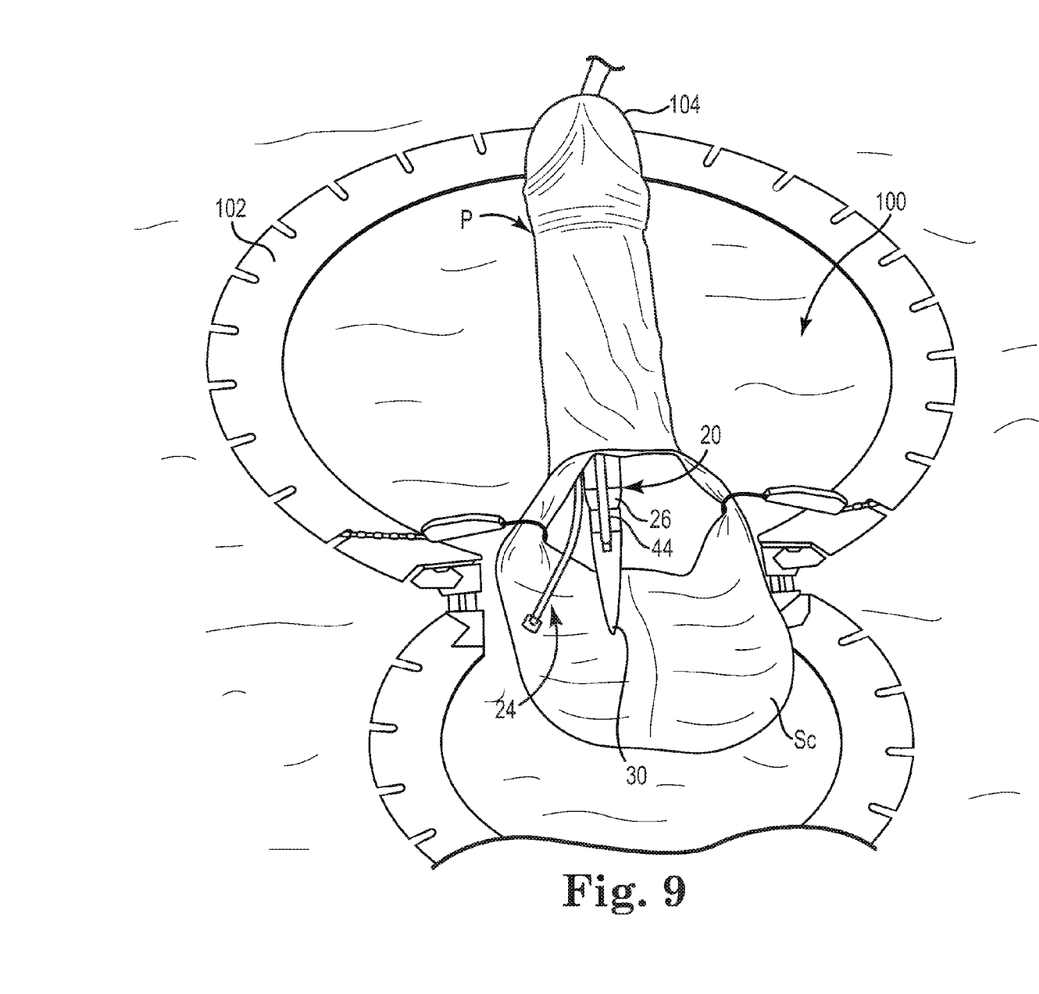
FIG. 9 is a schematic diagram of the patient with the penile prosthesis illustrated in FIG. 1 implanted distally into the penis.

FIG. 8 is a top view of a patient prepped and ready for implantation of a pair of the inflatable penile prostheses 22, and FIG. 9 is a top view of the patient having one inflatable penile prosthesis 22 inserted distally into one of the pair of copora cavernosa of the patient. The following description of FIGS. 8 and 9 refers to FIG. 1 (IPP 22 and tool 24) and FIGS. 6A-7C (expansion mechanisms 70 and 80, respectively).

The groin area 100 of the patient is shaved, cleaned and suitably prepped with a surgical solution prior to draping with a sterile drape. A retraction device, such as a retractor 102 sold under the trademark Lone Star and available from Lone Star Medical Products of Stafford, Tex., is placed around the penis P. Thereafter, the surgeon forms an incision to access the corpora covernosum of the patient, where suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc. As an example of the transverse scrotal approach, the surgeon forms a 2-3 cm transverse incision through the subcutaneous tissue of the median raphe of the upper scrotum Sc and dissects down through the Dartos fascia and Buck's fascia to expose the tunicae albuginea of the penis P. Thereafter, each corpora cavernosum is exposed in a corporotomy where a small (approximately 1.5 cm) incision is formed to allow the surgeon to access and subsequently dilate the corpora cavernosum. For example, the surgeon typically will insert an instrument (such as a blunt-ended scissors or other elongated tool) to separate a portion of the spongiosum material to open a path that allows insertion of a Furlow or other device to measure the proximal and distal length of the corpora cavernosum. Thereafter, the corpora cavernosum is dilated distally and proximally with a suitable expanding tool to create a space for IPP 22. For example, the surgeon begins dilation of both the distal and proximal corpora cavernosum by introducing an 8 mm dilator into the spongy tissue of the corpora with sequential progression to about a 14 mm dilator, each of which are introduced and pushed distally toward the glans penis and the crus of the penis, respectively. After dilation of the corpora cavernosum, the surgeon selects a proper length of IPP 22 (e.g., cylinder 26 and/or a rear tip extender 60) for implantation.

The primed and deflated sutureless cylinder 26 is inserted through the corporotomy with tool 24 after dilation of a first of the corpora cavernosa. As regards distal placement, for example, the distal end 40 of tool 24 is engage with opening 32 in tip 28 and the expansion mechanism 70 or 80 is expanded to engage with pocket 34. The tool 24 is thus connected to IPP 22 for placement of tip 28 into the dilated corpora cavernosum through the corporotomy. The surgeon employs tool 24 to push and direct distal tip 28 of IPP 22 to the distal-most portion of the corpora cavernosum. The surgeon may palpate the end of penis P at the subcoronal area 104 to locate the distal end of tip 28 to ensure proper placement of IPP 22 interior the corona of the glans penis of the patient. Notably, the sutureless cylinder 26 is thus located in the distal-most and portion of the corpora cavernosa without the use of a suture threaded through the glans penis. Thereafter, the expansion mechanism 70 or 80 is retracted and the distal end 40 of tool 24 is extracted from opening 32. The smooth and streamlined longitudinal shape of tool 24 permits the tool 24 to be removed from the corporotomy and away from IPP 22 with a reduced amount of drag. To this end, the tool 24 is configured to be removed from IPP 22 and the corporotomy in a manner that reduces the likelihood that the IPP 22 will be displaced away from the desired placement previously determined by the surgeon.

The proximal tip 30 of IPP 22 is implanted into the dilated proximal corpora cavernosum, which is typically completed after implantation of the distal tip 28 (the order of implantation is based on surgeon preference). For example, and with reference to FIGS. 4 and 5, in one embodiment distal end 40 of tool 24 is inserted into an opening provided in proximal tip 30. The expansion mechanism 70, 80 is expanded into the pocket (pocket 34' or pocket 64) that communicates with the opening, which allows tool 24 to guide the proximal to 30 of the IPP 22 proximally into the patient's corpora cavernosa toward a crus of the penis P.

After insertion of distal tip 28 and proximal tip 30 into the corpora cavernosum, the tool 24 is removed leaving IPP 22 inserted fully between the proximal and distal corpora cavernosum of the patient. The corporotomy is closed, and the remaining portions of the penile implantation of device, for example a reservoir and/or a pump, are implanted in the abdomen and scrotum S, respectively, of the patient.

Figure 10:
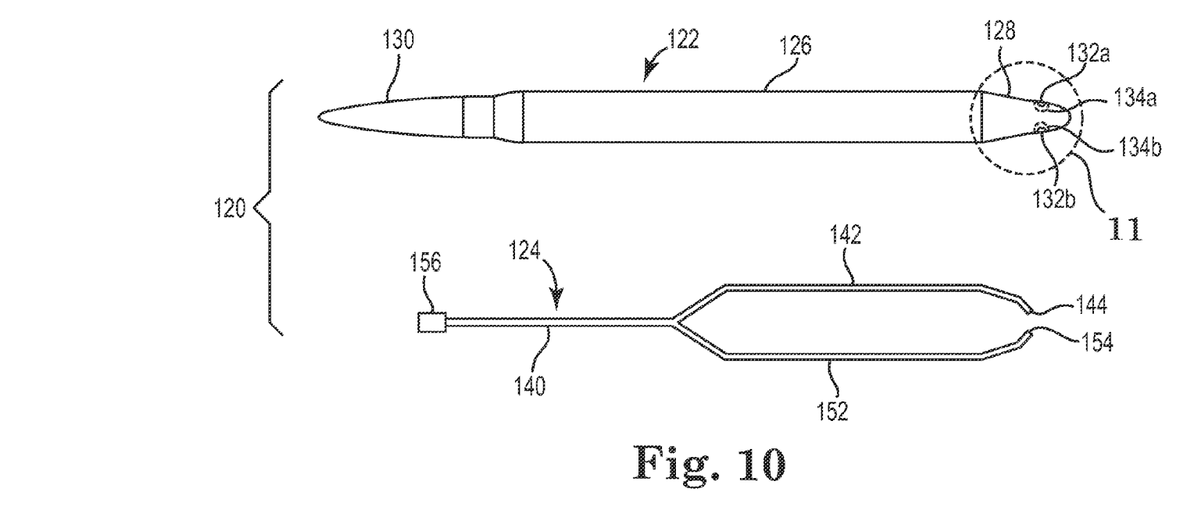
FIG. 10 is a top view of a system including an insertion tool configured to implant a penile prosthesis a male patient according to another embodiment.

FIG. 10 is a perspective view of a system 120 for implanting a penile prosthesis according to one embodiment. System 120 includes an implantable penile prosthesis 122 (IPP 122) and an insertion tool 124 configured to place IPP 122 into a corpora cavernosa of the patient.

In one embodiment, IPP 122 includes a cylinder 126 extending between a distal tip 128 and a proximal tip 130, where at least one of the distal tip 128 and the proximal tip 130 includes an opposed pair of openings 132a,b sized to receive insertion tool 124. Generally, cylinder 126 is similar to cylinder 26 described above, and tips 128, 130 are similar to tips 28, 30, respectively, as described above.

In an exemplary embodiment, tool 124 is provided as a bifurcated insertion tool including a central shaft 140, a first leg 142 extending from central shaft 140 and terminating in a first distal end 144, and a second leg 152 extending from central shaft 140 and terminating in a second distal end 154. In one embodiment, distal ends 144, 154 converge and are so configured to positively engage with openings 132a,b. In one embodiment, the bifurcated insertion tool 124 includes an inflatable bladder (similar to balloon 72 of FIGS. 6A, 6B) located within each of the first and second distal ends 144, 154 and includes a fluid inlet 156 coupled to a proximal end of central shaft 140 that communicates with the inflatable bladders.

Figure 11:
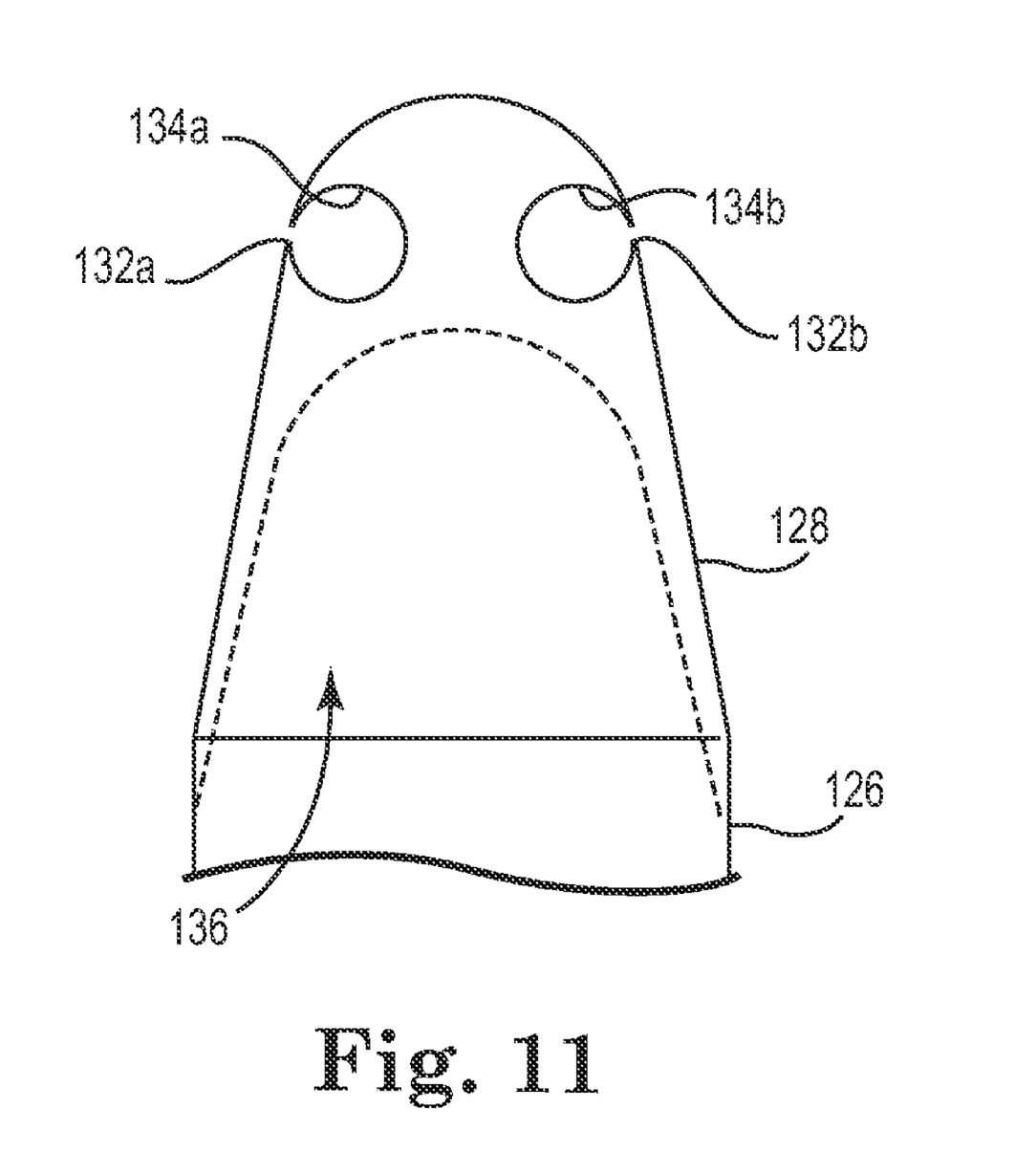
FIG. 11 is a cross-sectional view of a distal tip of the penile prosthesis illustrated in FIG. 10 according to one embodiment.

FIG. 11 is a side cross-sectional view of distal tip 128 illustrating first and second openings 132a,b that each communicates with a respective pocket 134a,b formed into distal tip 128. In one embodiment, distal tip 128 is formed (i.e., molded) from silicone, as an example, to define a cavity 136 that communicates with an interior of cylinder 126. Cylinder 126 is similar to cylinder 26, and openings 132a,b and their respective pockets 134a,b are similar to opening 32 and pocket 34 described above.

Tool 124 is configured to engage with the opposed pair of openings 132a,b to facilitate implanting IPP 122 into a distal end of the corpora cavernosum of the patient without the use of a suture. After distal ends 144, 154 of tool 124 are inserted into openings 132a,b a suitable fluid (a gas or a liquid) is introduced into inlet 156 to activate the expansion mechanism stowed within distal ends 144, 154. The expanded bladders are configured to engage with pockets 134a,b formed in distal tip 128 as the bladders expand out of the distal ends 144, 154, thus filling the pockets 134a,b and allowing tool 124 to positively engage with IPP 122.

Figure 12:
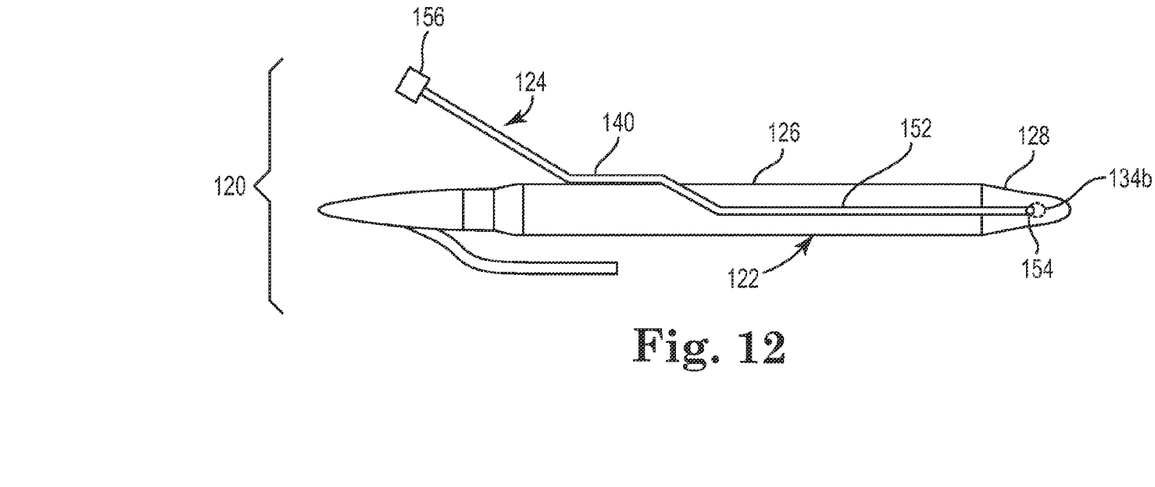
FIG. 12 is a side view of the insertion tool connected to the penile prosthesis illustrated in FIG. 10 according to one embodiment.

FIG. 12 a side view of system 120. The bifurcated insertion tool 124 straddles cylinder 126 when the distal ends 144, 154 are inserted into openings 130a,b (FIG. 10). In one embodiment, a fluid is introduced into inlet 156, where the fluid traverses the cannula formed by central shaft 140 and legs 142, 152 to expand a balloon or a bladder disposed in distal ends 144, 154. The expanding bladders fill pockets 134a,b to provide traction between tool 124 and IPP 122. In one embodiment, a pressure level of the fluid employed to expand the balloon is controlled, which allows control over the traction force established between tool 124 and IPP 122.

In one embodiment, bifurcated insertion tool and 24 is fabricated from stainless steel tubing provided with inlet port 156 on a proximal end and an expansion mechanism on distal ends 144, 154. In one embodiment, insertion tool and 24 is configured to cradle IPP 122 to facilitate insertion of IPP 122 into a dilated corpora cavernosum of the patient. It is to be understood that cylinder 126 is typically deflated or compressed prior to attachment of tool 124 to distal tip 128. In this regard, a spacing between opposing legs 142, 152 is selected to be narrow, for example 7-15 mm. A suitable length for insertion tool 124 is between approximately 12-24 mm, and one desirable length for insertion tool 124 is about 16 mm.

Insertion tool 124 has been described as including expansion balloons similar to the expansion mechanism described above in FIGS. 6A-6C. It is to be understood that insertion tool 124 may also be suitably fabricated to include a mechanical expansion mechanism similar to the expansion mechanism 80 described above in FIGS. 7A, 7B.

Embodiments of an implantable penile prosthesis system have been described that includes a tool having an expanding mechanism. The expanding mechanism is configured to engage with a pocket formed in the penile prosthesis, and the system coupled in this manner allows insertion of the prosthesis into a corpora of a penis without employing guide sutures in the glans penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable penile prosthesis system comprising:
a penile prosthesis comprising a cylinder extending between a distal tip and a proximal tip, at least one of the distal tip and the proximal tip having a pocket accessible by an opening, the pocket formed to extend laterally beyond a perimeter of the opening; and
an insertion tool comprising an expansion mechanism coupled to a distal end of the insertion tool;
wherein the opening is sized to receive the distal end of the insertion tool and the expansion mechanism is configured to expand into the pocket to couple the insertion tool with the penile prosthesis.

2. The system of claim 1, wherein each of the distal tip and the proximal tip have a pocket accessible by an opening.

3. The system according to claim 1, wherein the opening has a diameter and the pocket defines a recess having a width, a height, and a depth with at least one of the width and the height sized to be approximately two times larger than the diameter of the opening.

4. The system according to claim 1, wherein the expansion mechanism is selectively movable between a first state in which the expansion mechanism expands away from the distal end of the insertion tool and a second state in which the expansion mechanism is retractable into the distal end of the insertion tool.

5. The system according to claim 1, further comprising a suture hole formed in the distal tip, the suture hole having a suture hole axis substantially orthogonal to a longitudinal axis of the cylinder.

6. The system according to claim 1, wherein the insertion tool comprises a cannula and the expansion mechanism comprises a balloon disposed in the cannula, the balloon inflatable to expand into the pocket.

7. The system according to claim 1, wherein the expansion mechanism comprises at least one mechanically extensible finger that is configured to move laterally beyond the distal end of the insertion tool.

8. The system according to claim 1, further comprising:
a rear tip extender attachable to the proximal tip of the penile prosthesis, the rear tip extender defining a second opening and a second pocket that extends laterally beyond a boundary of the second opening.

9. The system according to claim 1, wherein the insertion tool comprises a bifurcated insertion tool comprising a central shaft, a first leg extending from the central shaft and terminating in a first distal end, and a second leg extending from the central shaft and terminating in a second distal end, each of the first and second distal ends comprising an expansion mechanism that is configured to expand into one of a pair of pockets formed in the penile prosthesis.

10. The system according to claim 1, wherein the opening comprises a substantially circular perimeter and the pocket defines a substantially spherical recess communicating with the opening, a diameter of the spherical recess greater than a diameter of the circular perimeter.

11. An insertion tool configured for implanting a penile prosthesis into a patient, the insertion tool comprising:
an expansion mechanism coupled to a distal end of the insertion tool that is configured to expand out of the distal end of the tool into a pocket formed in the penile prosthesis.

12. The insertion tool of claim 11, wherein the expansion mechanism is selectively movable between a first state in which the expansion mechanism expands away from the distal end of the insertion tool and a second state in which the expansion mechanism is retractable into the distal end of the insertion tool.

13. The insertion tool according to claim 11, wherein the insertion tool comprises a cannula and the expansion mechanism comprises a balloon disposed in the cannula, the balloon inflatable to expand into the pocket.

14. The insertion tool according to claim 13, wherein the balloon comprises a polyester balloon.

15. The insertion tool according to claim 11, wherein the expansion mechanism comprises at least one mechanically extensible finger that is configured to move laterally beyond the distal end of the insertion tool.

16. The insertion tool according to claim 11, wherein the insertion tool comprises a bifurcated insertion tool comprising a central shaft, a first leg extending from the central shaft and terminating in a first distal end, and a second leg extending from the central shaft and terminating in a second distal end, each of the first and second distal ends comprising an expansion mechanism that is configured to expand into a one of a pair of pockets formed in the penile prosthesis.

17. The insertion tool according to claim 11, wherein the expansion mechanism is configured to expand out of the distal end of the tool and into a pocket formed in a distal tip of the penile prosthesis.

18. The insertion tool according to claim 11, wherein the expansion mechanism is configured to expand out of the distal end of the tool and into a pocket formed in a proximal tip of the penile prosthesis.

19. The insertion tool according to claim 11, wherein the expansion mechanism is configured to expand out of the distal end of the tool and into a pocket formed in a rear tip extender that is attachable to a proximal tip of the penile prosthesis.

20. An implantable penile prosthesis comprising:
a cylinder extending between a distal tip and a proximal tip, at least one of the distal tip and the proximal tip having an opening communicating with a pocket that is formed to extend laterally beyond a perimeter of the opening.

21. The implantable penile prosthesis of claim 20, wherein the cylinder comprises an inflatable cylinder.

22. The implantable penile prosthesis according to claim 20, wherein the distal tip has the opening communicating with the pocket.

23. The implantable penile prosthesis according to claim 20, wherein the proximal tip has the opening communicating with the pocket.

24. The implantable penile prosthesis according to claim 20, wherein the opening has a diameter and the pocket defines a recess having a width, a height, and a depth with at least one of the width and the height sized to be approximately two times larger than the diameter of the opening.

25. The implantable penile prosthesis according to claim 20, wherein the pocket is formed as a substantially spherical space.

26. The implantable penile prosthesis according to claim 20, further comprising a suture hole formed in the distal tip, the suture hole having a suture hole axis substantially orthogonal to a longitudinal axis of the cylinder.

27. The implantable penile prosthesis according to claim 20, further comprising:
a rear tip extender attachable to the proximal tip of the penile prosthesis, the rear tip extender defining a second opening and a second pocket that extends laterally beyond a boundary of the second opening.

28. The implantable penile prosthesis according to claim 20, wherein the proximal tip is integrally formed with the cylinder and the distal tip is attached as a separate component to the cylinder of the penile prosthesis.

* * * * *